United States Patent [19]

Thaman et al.

[11] Patent Number: 4,891,228

[45] Date of Patent: *Jan. 2, 1990

[54] MEDICATED CLEANSING PADS

[75] Inventors: Lauren A. Thaman, Milford; James P. SaNogueira, Newtown; Teresa M. Petraia, Ansonia, all of Conn.

[73] Assignee: Richardson-Vicks Inc., Wilton, Conn.

[*] Notice: The portion of the term of this patent subsequent to Jan. 2, 2007 has been disclaimed.

[21] Appl. No.: 151,338

[22] Filed: Feb. 2, 1988

[51] Int. Cl.⁴ .............................................. C01B 31/26
[52] U.S. Cl. .................................... 424/443; 424/446; 428/295
[58] Field of Search .................. 424/78, 484, 443–449; 428/295

[56] References Cited

U.S. PATENT DOCUMENTS

| | | |
|---|---|---|
| Re. 28,957 | 9/1976 | Drelich et al. ...................... 428/198 |
| 3,706,595 | 12/1972 | Drelich et al. . |
| 3,778,341 | 12/1973 | Plummer et al. . |
| 4,341,213 | 7/1982 | Cohen . |
| 4,505,924 | 3/1985 | Taylor et al. . |
| 4,514,385 | 4/1985 | Damani et al. ...................... 424/81 |
| 4,719,226 | 1/1988 | Otsuka et al. ...................... 514/449 |
| 4,738,848 | 4/1988 | Yoshida et al. ...................... 424/448 |

OTHER PUBLICATIONS

Reidel, J. E., "Nonwoven Bonding Methods & Materials", *Nonwoven World*, (1987), pp. 47–50.

*Primary Examiner*—Nancy A. B. Swisher
*Attorney, Agent, or Firm*—David K. Dabbiere; Douglas C. Mohl; Jack D. Schaeffer

[57] ABSTRACT

Disclosed are medicated cleansing pads comprising: (a) from about 50% to about 75% of a nonwoven fabric material; (b) from about 20% to about 75% (on a dry solids basis) of a water soluble polymeric resin of the formula:

$$(A_x)_m (B_y)_n$$

wherein A is one or more monomers selected from styrene or styrene derivatives and B is one or more monomers selected from butadiene or butadiene derivatives, x is the number of different A monomer components present in the copolymer chain, with x being an integer of 1 or more and y is the number of B monomer components present in the copolymer chain, with y being an integer of 0 or more and m:n is the weight ratio of A monomer components to B monomer components, and is from about 10:1 to about 1:5, preferably from about 5:1 to about 1:2, and (c) from about 0.1% to about 50% of salicylic acid active composition.

17 Claims, No Drawings

MEDICATED CLEANSING PADS

TECHNICAL FIELD

This invention relates to medicated cleansing pads which contain a salicylic acid active composition, and also to methods for treating acne.

BACKGROUND OF THE INVENTION

Acne is a common inflammatory pilobaceous disease characterized by comedones, papules, pustules, inflamed nodules, superficial pus-filled cysts, and in extreme cases, sinus formation and deep inflammation, sometimes associated with purulent sacs.

The pathogenesis of acne is complex. An interaction between hormones, keratinization, sebum and bacteria somehow determines the course and severity of the disease. Acne begins at puberty when the increase of androgens causes an increase in the size and activity of the pilosebaceous glands. The earliest microscopic change is intrafollicular hyperkeratosis, which leads to restriction of the pilosebaceous follicle with consequent formation of the comedo composed of sebum, keratin, and microorganisms, particularly Propionibacterium (Corynebacterium) acnes. Lipases from P. acnes break down triglycerides in the sebum to form free fatty acids (FFA), which irritate the follicular wall. Retention of sebaceous secretions and dilation of the follicle may lead to cyst formation. Rupture of the follicle with release of the contents into the tissues induces an inflammatory reaction which heals with scarring in severe cases.

Acne tends to appear during puberty and to fade away, usually spontaneously when growth has stopped. Only rarely does it recede before the age of 20 and occasionally it is still to be found at the age of 30 and beyond. The face is the favorite location affected and in severe cases the alterations cause considerable disfigurement, and make the physical burden of the afflicted person easy to understand.

Acne can be treated by topical application of various lotions, salves and the like or by, for example, localized treatment with, for example, sulphur, resorcinol, salicylic acid, benzoyl peroxide or vitamin A acids.

Salicylic acid is a well recognized anti-acne active ingredient which causes a reduction in intercellular cohesion of the corneocytes (see C. Huber et al, Arch. Derm. Res. 257, 293-297, 1977), thereby dissolving the existing keratin plugs as well as preventing the formation of new ones. In order to best exert its keratolytic and comedolytic effect, the ideal anti-acne composition should deliver and retain optimal concentrations of salicylic acid in the stratum corneum with less penetration through the skin and into the general circulation.

A common method of treating acne is by application of a cleansing pad which contains salicylic acid. However, such pads have proven not totally satisfactory because they have little loft, lack rigidity and are unsatisfactory carriers of the anti-acne salicylic acid active. Also, such pads have unsatisfactory cosmetics which hinder their effectiveness.

In order to improve loft, carded or air-laid fabrics must be used. Such fabrics require a resin be incorporated into the pad; however many resins cause degradation of the salicylic acid active thereby hindering efficacy. Additionally, it has been found that the pads of the present invention deliver high levels of active and provide improved efficacy for, for example, cleansing and oil absorbency.

It is therefore an object of the present invention to provide a pad with improved aesthetics and also improved efficacy. Specifically, it is an object of the present invention to provide a pad with high degree of loft, greater cleansing capability, and oil removal and improved rigidity.

SUMMARY OF THE INVENTION

The present invention relates to medicated cleansing pads comprising:
 (a) from about 50% to about 75% of a nonwoven fabric material;
 (b) from about 20% to about 75% (on a dry solids basis) of a water soluble polymeric resin of the formula:

$$(A_x)_m(B_y)_n$$

wherein A is one or more monomers selected from styrene or styrene derivatives and B is one or more monomers selected from butadiene or butadiene derivatives, x is the number of different A monomer components present in the copolymer chain, with x being an integer of b 1 or more and y is the number of B monomer components present in the copolymer chain, with y being an integer of 0 or more and m:n is the weight ratio of A monomer components to B monomer components, and is from about 10:1 to about 1:5, preferably from about 5:1 to about 1:2; and
 (c) from about 0.1% to about 50% of salicylic acid active composition.

This invention also encompasses a method of treating acne in humans and lower animals comprising topically applying to the affected area the medicated pads of the present invention.

DETAILED DESCRIPTION OF THE INVENTION

The medicated pads of the present invention comprise non-woven fibers containing a styrene or styrene-butadiene resin, or derivative thereof along with a salicylic acid active composition. Such pads can have a variety of textural features, running anywhere from a coarse to a smooth surface.

The composition and method of the present invention are suitable for the treatment of various dermatological disorders such as psoriasis, idiopathic vitiligo, seborrheic dermatitis and bullous pemphigoid, especially for the treatment of acne. As described in Dermatology, Third Edition, the c. V. Mosby Company, St. Louis (1974), in Chapter 6, notably at page 91, the clinical lesions which typify acne include comedones, papules, pustules, cysts, and scars.

STRUCTURAL FIBERS

Although not limited thereto, the present invention contains nonwoven fabrics derived from "oriented" or carded fibrous webs composed of textile-length fibers, the major proportion of which are oriented predominantly in one direction.

The convention base starting material for the majority of these nonwoven fabrics is usually a fibrous web comprising any of the common textile-length fibers, or mixtures thereof, the fibers varying in average length from approximately ½ inch to about 3 inches, preferably 1½ to 2 inches. Exemplary of such fibers are the natural fibers such as cotton and wool and the synthetic or man-made cellulosic fibers, notably rayon or regenerated cellulose. Such as those supplied by BASF.

Other textile-length fibers of a synthetic or man-made origin may be used in various proportions to replace either partially or perhaps even entirely the previously-named fibers. Such other fibers include: polyamide fibers such as nylon 6, nylon 66, nylon 610, etc.; polyester fibers such as "Dacron", "Fortrel" and "Kodel"; acrylic fibers such as "Acrilan", "Orlon" and "Creslan"; modacrylic fibers derived from polyethylene and polypropylene; cellulose ester fibers such as "Arnel" and "Acele"; polyvinyl alcohol fibers, etc.

These textile-length fibers may be replaced either partially or entirely by fibers having an average length of less than about one-half inch and down to about one-quarter inch. These fibers, or mixtures, thereof, are customarily processed through any suitable textile machinery (e.g., a conventional cotton card, a "Rando-Webber" a paper-making machine, or other fibrous web producing apparatus) to form a web or sheet of loosely associated fibers, weighing from about 100 grains to about 2,000 grains per square yard or even higher.

If desired, even shorter fibers, such as wood pulp fibers or cotton linters, may be used in varying proportions, even up to 100%, where such shorter length fibers can be handled and processed by available apparatus. Such shorter fibers have lengths less than ¼ inch.

The resulting fibrous web or sheet, regardless of its method of production, is then subjected to at least one of several types of bonding operations to anchor the individual fibers together to form a self-sustaining web incorporating the resins described infra. One method is to impregnate the fibrous web over its entire surface area with the resins of the present invention. Such overall impregnation produces a nonwoven fabric of good longitudinal and cross strength, acceptable durability and solvent resistable and satisfactory abrasion resistance.

Methods of making nonwoven cloths are not a part of this invention and, being well known in the art, are not described in detail herein. Generally, however, such cloths are made by air- or water-laying processes in which the fibers or filaments are first cut to desired lengths from long strands, passed into a water or air stream, and then deposited onto a screen through which the fiber-laden air or water is passed. The deposited fibers or filaments are then adhesively bonded together, using the resins of the present invention, dried, cured, and otherwise treated as desired to form the nonwoven cloth.

The preferred nonwoven cloth substrates used in the invention herein are generally adhesively bonded fibers or filamentous products having a web or carded fiber structure (when the fiber strength is suitable to allow carding) or comprising fibrous mats in which the fibers or filaments are distributed haphazardly or in random array (i.e., an array of fibers in a carded web where partial orientation of the fibers is frequently present, as well as a completely haphazard distributional orientation), or substantially aligned. The fibers or filaments can be natural (e.g., wool, silk, jute, hemp, cotton, linen, sisal, or ramie) or synthetic (e.g., rayon, cellulose ester, polyvinyl derivatives, polyolethins, polyamides, or polyesters) as have been described hereinabove. These nonwoven materials are generally described in Riedel, "Nonwoven Bonding Methods and Materials", *Nonwoven World*, (1987).

The absorbent properties preferred herein are particularly easy to obtain with nonwoven cloths and are provided merely by building up the thickness of the cloth, i.e., by superimposing a plurality of carded webs or mats to a thickness adequate to obtain the necessary absorbent properties, or by allowing a sufficient thickness of the fibers to deposit on the screen. Any diameter or denier of the fiber (generally up to about 15 denier) can be used, inasmuch as it is the free space between each fiber that makes the thickness of the cloth directly related to the absorbent capacity of the cloth. Thus, any thickness necessary to obtain the required absorbent capacity can be used.

WATER SOLUBLE RESIN

The binder-resins used in the manufacture of the nonwoven cloths of the present invention provide substrates possessing a variety of desirable traits. In addition to improved loft and rigidity, there is virtually no degradation of the salicylic acid active component used in the anti-acne pads of the present invention. Additional benefits provided by these resins include excellent strength in all directions resulting in pads which are not prone to tear or separate in normal use. Resins, or polymers as they are often referred to, useful in the present invention are high molecular weight organic compounds and are of a synthetic or man-made origin. The resins useful in the present invention are formed from styrene monomers or styrene and butadiene monomer units and are formed usually either by addition or condensation of one or more monomers. The resins have the general formula:

$$(A_x)_m(B_y)_n$$

wherein A is one or more monomers selected from styrene or styrene derivatives and B is one or more monomers selected from butadiene or butadiene derivatives, x is the number of different A monomer components present in the copolymer chain, with x being an integer of 1 or more and y is the number of B monomer components present in the copolymer chain, with y being an integer of 0 or more and m:n is the weight ratio of A monomer components to B monomer components, and is generally within the range of from about 10:1 to about 1:5, preferably from about 5:1 to about 1:2.

Suitable examples of such styrene or butadiene monomer units include 1,2 butadiene, 1,4 butadiene, 2-ethyl-1,3 butadiene isoprene, high, medium and carboxylated butadiene, 2 methyl styrene, 3 methyl styrene, 4 methyl styrene, ethyl styrene, butyl styrene, and 2,3 dimethyl butadiene.

The resins of the present invention may be used either as homopolymers comprising a single repeating monomer unit, or they may be used as copolymers comprising two, three or more different monomer units which are arranged in random fashion, or in a definite order alternating fashion, within the polymer chain (block copolymers). Also included within the inventive concept are the block polymers comprising relatively long blocks of different monomer units in a polymer chain and graph polymers comprising chains of one monomer attached to the backbone of another polymer chain. These polymers are fully described in Noshay et al.

The resins of the present invention have a glass transition temperature range of from about −100° C. to about 200° C., preferably from about −40° C. to about 50° C.

Also preferred is that the resins of the present invention have a pH of about 7 or higher, preferably from 7.5 to about 9.

These styrene and styrene butadiene resins are generally described in *Introduction to Polymer Science and Technology: An SPE Textbook*, H. S. Kaufman et al., John Wiley & Sons, New York (1977); *Principles of Polymerization*, G. Odian, John Wiley & Sons, New York (1981); and in *Block Copolymers Overview and Critical Survey*, A. Noshay et al., Academic Press, New York (1977), all of which are incorporated by reference.

The deposition of the synthetic resin binder particles on the individual fibers may be accomplished in many ways at various points in the manufacture process of the pad, such as by stock chest deposition techniques. Such techniques generally include the formation of a substantially uniform, aqueous slurry of the fibers which will make up the fibrous web and inclusion in the aqueous slurry of the synthetic resin particles which are to be deposited on and adhered to the individual fibers. Deposition aids may be used, if necessary, to promote the deposition and adherence of the synthetic resin particles on the particular fibers. Examples of such deposition aids are Rohm & Haas deposition aid S-243, polyethylene amine, alum, polymeric amines, polymeric amides, cationic starch, etc. Methods of forming such nonwoven textile fabrics are disclosed in, for example, U.S. Pat. No. 3,778,341 to Plummer, et al., assigned to Johnson & Johnson, issued Dec. 11, 1973.

ACTIVE COMPOSITION

The salicylic acid active composition can be salicylic acid alone, salicylic acid derivatives, and salicylic acid in combination with other active ingredients such as benzoyl peroxide, sulfur, resorcinol, derivatives of retinoic acid, chlorhydroxyquinoline, hormonal and antibacterial agents, and the like. Most preferred is salicylic acid in a hydroalcoholic solution.

Salicylic acid is a well known anti-acne component and is generally described in U.S. Pat. No. 4,514,385, to Damani, et al., assigned to Alcon Laboratories, issued Apr. 30, 1985.

The preferred anti-acne active composition comprises a hydroalcoholic solution at pH 2 to 4 of salicylic acid as the active anti-acne ingredient together with a specific anionic surfactant component. More preferably such active is a stable, hydroalcoholic composition having a pH value of from 2 to 4 and containing from about 0.2 to about 5.0 percent by weight of salicylic acid and from about 0.2 to about 5.0 percent by weight of sodium methyl cocoyl taurate and/or sodium methyl oleoyl taurate as the anionic surfactant component. Generally, a sufficient amount of a cosmetically acceptable alkaline component (i.e., alkalizing agent) to provide and maintain the composition with a pH from about 2.0 to about 4 is included.

As the alcohol component of the hydroalcoholic solvent, from about 10 to about 60 percent by weight of ethyl alcohol, measured as total $C_2H_5OH$ content, is preferred although a like amount of isopropyl alcohol ($C_3H_7OH$) may also be beneficially utilized. From about 30 to about 80 percent by weight of water is also required as the aqueous component of the hydroalcoholic solvent.

As noted previously, salicylic acid is a well known active anti-acne ingredient. A listing of commercially available anti-acne products containing salicylic acid will be found in the Physician's Desk Reference for Nonprescription Drugs, 7th Edition, 1986, page 314.

The anionic surfactant component of this active composition, i.e., the taurate surfactant component, is specifically directed to sodium methyl cocoyl taurate and sodium methyl oleoyl taurate, both of which are readily available from diverse commercial suppliers, as noted in The Cosmetic, Toiletry and Fragrance Association (CTFA) Cosmetic Ingredient Dictionary, 3rd Edition, 1982, pages 286–287.

Although it is preferred to use the taurate surfactant as the sole surfactant in the active compositions, other surfactants may be included, the nonionic type having preference over the anionic type in view of the relative non-irritating characteristic to the skin of the former. Cationic type surfactants, which are most irritating to the skin, are less preferred because of their marked susceptibility to hydrolysis as the low acidic pH of the subject compositions.

The pH value of the preferred active component, from about 2 to about 3.5, may be achieved by use of appropriate cosmetically acceptable primary or dual buffer systems. In most instances, the resultant pH of the hydroalcoholic solution of salicylic acid is slightly below or at the lower end of the indicated range, and all that is required to adjust the pH to a desired higher value within the indicated range is to add an alkaline additive such as is commonly utilized in cosmetic formulations for such purpose. Although sodium carbonate is preferred, other suitable alkalizing agents include potassium carbonate, sodium hydroxide, potassium hydroxide, triethanolamine and the like. If deemed necessary to change or adjust the pH to a lower value, a suitable cosmetically acceptable acidifying agent such as citric acid may be employed.

OPTIONAL COMPONENTS

The salicylic composition present on the pads of the present invention may also include optional additives such as, for example, antibacterial agents such as benzyl alcohol or methyl paraben; antioxidants and preservatives such as ethylenediamine tetraacetic acid; astringents such as witch hazel; odorants and sensates such as camphor or menthol; colorants and other cosmetically acceptable adjuvants generally utilized in topical anti-acne compositions. Obviously, the choice and amount of any additional ingredient should be such that said ingredient does not deleteriously counterbalance the beneficial characteristics herein ascribed to the medicated pads.

EXAMPLE I

A medicated pad of the present invention is made as follows:

| Pad Composition | Weight % |
| --- | --- |
| Rayon (denier = 8)[1] | 32.5 |
| Polyester (denier = 15)[2] | 32.5 |
| Styrene-butadiene resin[3] | 35.0 |

| Active Composition | Weight % |
| --- | --- |
| Salicylic acid | 2% |
| SD-40 Ethanol | 40% |

-continued

| | |
|---|---|
| Water | 58% |

[1] Obtained from BASF Wyandotte.
[2] Obtained from Eastern Chemical Company
[3] Obtained from UNOCAL 76 as 76 RES 4170

A fibrous card web weighing about 67 grams per square yard made up of the rayon and polyester and the styrene butadiene resin containing a ratio of styrene to butadiene of 65:35 is passed through the nip of nip rolls as is known to one skilled in the art. The resulting nonwoven fabric material has a loft of 72 mills. The material is then cut into a circular shape (diameter of 7 cm).

The active components are combined to form a solution and the pad composition is saturated in this solution.

Application of the resulting medicated pad twice a day to a person in need of anti-acne treatment increases keratinization of the stratum corneum.

EXAMPLE II A medicated pad of the present invention is made as follows:

| Pad Composition | Weight % |
|---|---|
| Rayon (denier = 1.5)[1] | 78.0 |
| Styrene-butadiene resin[2] | 22.0 |

| Active Composition | Weight % |
|---|---|
| Salicylic acid | 0.5 |
| $C_2H_5OH$ | 20.0 |
| Sodium methyl cocoyl taurate | 1.0 |
| Water | 78.5 |

[1] Obtained from Leight Corporation
[2] Obtained from UNOCAL 76 as 76 RES 4305

The styrene-butadiene resin containing a ratio of styrene to butadiene of 45:55 is laid on a fibrous card web utilizing an engraved print roll and is passed through a nip and passed on to a series of dry cans. This results in a nonwoven material weighing about 36 grams per square yard. The resulting non-woven fabric has a loft of about 12 mills. The material is then cut into a square shape with edges of 5 cm.

The active components are combined to form a solution and the pad composition is saturated in this solution.

Application of the resulting medicated pad twice a day to a person in need of anti-acne treatment increases keratinization of the stratum corneum.

EXAMPLE III

| Pad Composition | Weight % |
|---|---|
| Polyester (denier = 1.5)[1] | 35 |
| Rayon (denier = 3.0)[2] | 35 |
| Styrene-butadiene resin[3] | 30 |

| Active Composition | Weight % |
|---|---|
| Salicylic acid | 2.00 |
| Sodium methyl cocoyl taurate | 0.72 |
| $C_2H_5OH$ (95% ethanol) | 35.00 |
| Witch hazel distillate | 5.00 |
| Quaternium-22 | 0.60 |
| Aloe vera gel | 0.50 |
| Menthol | 0.05 |
| Camphor | 0.001 |
| Flavoring sensate oils | 0.001 |

-continued

| | |
|---|---|
| Water | 56.128 |

[1] Obtained from DuPont Chemical Company
[2] Obtained from Avteck
[3] Obtained from UNOCAL 76 as 76 RES 5550 (ratio of styrene to butadiene of 45:55)

The components are combined as described above in Example II. The resulting pad has a loft of 23 mills and a basis weight of 46 grams per square yard. The pads were then cut into a racetrack oval pad 6 cm by 5.5 cm.

What is claimed is:

1. A medicated cleansing pad comprising:
   (a) from about 50% to about 75% by weight of one layer of a nonwoven fabric material;
   (b) from about 20% to about 75% by weight (on dry solids basis) of a water soluble polymeric resin of the formula:

$$(A_x)_{m}(B_y)_{n}$$ 

wherein A is one or more monomers selected from styrene or styrene derivatives and B is one or more monomers selected from butadiene or butadiene derivatives, x is the number of different A monomer components present in the copolymer chain, with x being an integer of 1 or more and y is the number of B monomer components present in the copolymer chain, with y being an integer of 0 or more and m:n is the weight ratio of A monomer components to B monomer components, and is from about 10:1 to about 1:5; and
   (c) from about 0.1% to about 50% by weight of salicylic acid active composition.

2. A medicated cleansing pad according to claim 1 wherein said nonwoven material is selected from the group consisting of polyester and rayon and mixtures thereof.

3. A medicated cleansing pad according to claim 2 wherein said nonwoven material has a denier of from about 1 to about 15 and a loft of from about 1 to about 200 mills.

4. A method of treating acne in humans and lower animals comprising topically applying to the affected area the pad of claim 3.

5. A medicated pad according to claim 3 wherein said polymeric resin comprises from about 20% to about 60% by weight of the pad.

6. A medicated pad according to claim 5 wherein said resin is comprised of styrene monomers and butadiene monomers and derivative thereof.

7. A medicated pad according to claim 6 wherein the weight ratio of styrene to butadiene is from about 5:1 to about 1:2.

8. A medicated pad according to claim 7 wherein comprises from about 0.1 to about 5.0% by weight of the salicylic acid composition.

9. A medicated pad according to claim 8 which comprises from about 0.5% to about 2.0% by weight of the salicylic acid composition.

10. A medicated pad according to claim 9 wherein the salicylic acid active component comprises:
   (a) from about 0.2 to about 5.0 weight percent of salicylic acid;
   (b) from about 10 to about 60 weight percent of $C_2H_5OH$ or $C_3H_7OH$;
   (c) from about 30 to about 80 weight percent of water; and (d) from about 0.2 to about 5.0 weight percent of sodium methyl cocoyl taurate or sodium methyl oleoyl taurate; the said active composition having a pH value of from about 2 to about 3.5.

11. A medicated pad according to claim 10 wherein (b) is $C_2H_5OH$ and (d) is sodium methyl cocoyl taurate.

12. A medicated pad according to claim 11 which comprises from about 20% to about 60% by weight of the resin component.

13. A medicated pad according to claim 10 wherein (b) is $C_2H_5OH$ and (d) is sodium methyl oleoyl taurate.

14. A method of treating acne in humans and lower animals comprising topically applying to the affected area the pad of claim 13.

15. A medicated pad according to claim 10 which comprises from about 20% to about 50% by weight of the resin component.

16. A method of treating acne in humans and lower animals comprising topically applying to the affected area the pad of claim 10.

17. A method of treating acne in humans and lower animals comprising topically applying to the affected area the pad of claim 1.

* * * * *